US009269950B2

(12) United States Patent
Geoffroy et al.

(10) Patent No.: US 9,269,950 B2
(45) Date of Patent: Feb. 23, 2016

(54) PROCEDURE TO OPTIMIZE MATERIALS FOR CATHODES AND CATHODE MATERIAL HAVING ENHANCED ELECTROCHEMICAL PROPERTIES

(71) Applicants: CLARIANT (CANADA) INC., Toronto (CA); BATHIUM CANADA INC., Boucherville (CA)

(72) Inventors: Denis Geoffroy, Verdun (CA); Guoxian Liang, St-Hyacinthe (CA); Michel Gauthier, La Prairie (CA); Thorsten Lahrs, Bad Vilbel (DE); Nathalie Ravet, Montreal (CA); Michel Parent, St-Jean-sur-Richelieu (CA); Alain Vallee, Varennes (CA); Patrick Leblanc, Boucherville (CA); Frederic Cotton, Montreal (CA)

(73) Assignees: JOHNSON MATTHEY PUBLIC LIMITED COMPANY, London (GB); BATHIUM CANADA INC., Quebec (CA)

( * ) Notice: Subject to any disclaimer, the term of this patent is extended or adjusted under 35 U.S.C. 154(b) by 479 days.

(21) Appl. No.: 13/693,908

(22) Filed: Dec. 4, 2012

(65) Prior Publication Data
US 2013/0095390 A1    Apr. 18, 2013

Related U.S. Application Data

(63) Continuation of application No. 13/575,917, filed as application No. PCT/CA2011/000108 on Jan. 28, 2011, now abandoned.

(51) Int. Cl.
| | |
|---|---|
| *H01M 4/136* | (2010.01) |
| *H01M 4/1397* | (2010.01) |
| *G01N 33/20* | (2006.01) |
| *H01M 10/0565* | (2010.01) |
| *H01M 4/36* | (2006.01) |
| *H01M 4/58* | (2010.01) |
| *C01B 25/45* | (2006.01) |
| *H01M 10/052* | (2010.01) |

(52) U.S. Cl.
CPC .............. *H01M 4/136* (2013.01); *C01B 25/45* (2013.01); *G01N 33/20* (2013.01); *H01M 4/366* (2013.01); *H01M 4/5825* (2013.01); *H01M 4/1397* (2013.01); *H01M 10/052* (2013.01); *H01M 10/0565* (2013.01); *Y02E 60/122* (2013.01)

(58) Field of Classification Search
CPC ...... C01B 25/45; G01N 33/20; H01M 10/052; H01M 10/0565; H01M 4/136; H01M 4/1397; H01M 4/366; H01M 4/5825; Y02E 60/122
See application file for complete search history.

(56) References Cited

U.S. PATENT DOCUMENTS

| | | | |
|---|---|---|---|
| 5,910,382 A | 6/1999 | Goodenough et al. | |
| 6,514,640 B1 | 2/2003 | Armand et al. | |
| 6,855,273 B2 | 2/2005 | Ravet et al. | |
| 6,962,666 B2 | 11/2005 | Ravet et al. | |
| 7,344,659 B2 | 3/2008 | Ravet et al. | |
| 7,457,018 B2 | 11/2008 | Armand et al. | |
| 2002/0124386 A1 | 9/2002 | Hosoya et al. | |
| 2002/0195591 A1 | 12/2002 | Ravet et al. | |
| 2004/0157126 A1 | 8/2004 | Belharouak et al. | |
| 2007/0134554 A1 | 6/2007 | Armand et al. | |
| 2009/0104537 A1 | 4/2009 | Deschamps | |
| 2009/0162754 A1 | 6/2009 | Cotton et al. | |
| 2010/0297496 A1 | 11/2010 | Ravet et al. | |
| 2011/0017947 A1 | 1/2011 | Nuspl et al. | |
| 2011/0068295 A1* | 3/2011 | Beck et al. ................. | 252/182.1 |
| 2011/0097479 A1 | 4/2011 | Ravet et al. | |
| 2012/0028121 A1 | 2/2012 | Gauthier et al. | |

FOREIGN PATENT DOCUMENTS

| | | |
|---|---|---|
| CA | 2307119 A1 | 10/2000 |
| CA | 2667602 A1 | 5/2008 |
| CN | 1722497 A | 1/2006 |
| CN | 101558517 A | 10/2009 |
| EP | 1049182 A2 | 11/2000 |
| FR | 2881275 A1 | 7/2006 |
| JP | 2002-117848 A | 4/2002 |

(Continued)

OTHER PUBLICATIONS

Supplemental European Search Report for EP 11 73 6573 dated Nov. 4, 2014.
Julien et al. "Nanoscopic Scale Studies of LiFePO$_4$ as Cathode Material in Lithium-Ion Batteries for HEV Application", IONICS, 13:395-411 (2007).
International Search Report (PCT/ISA/210) mailed on Apr. 21, 2011, by the Canadian Intellectual Property office as the International Searching Authority for International Application No. PCT/CA2011/000108. 6 pages.

(Continued)

*Primary Examiner* — Carlos Barcena
(74) *Attorney, Agent, or Firm* — Marshall, Gerstein & Borun LLP

(57) ABSTRACT

A material C-A$_x$M(XO$_4$)$_y$ that is of particles of a compound of the formula A$_x$M(XO$_4$)$_y$, wherein said particles include a carbon deposit deposited by means of pyrolysis on at least a portion of the surface thereof, and where: A is Li alone or partially replaced by at most 10 atomic % of Na or K; M is Fe(II), or Mn(II), or mixtures thereof alone or partially replaced by at most 30 atomic % of one or more metals selected from Mn, Ni and Co and/or at most 5% of Fe(III); XO$_4$ is PO$_4$ alone or partially replaced by at most 10 molar % of at least one group selected from SO$_4$, SiO$_4$ and MoO$_4$; and where said material has a calcium impurity content of lower than about 1000 ppm.

24 Claims, No Drawings

(56) References Cited

FOREIGN PATENT DOCUMENTS

| | | | |
|---|---|---|---|
| JP | 2003-292307 A | 10/2003 | |
| JP | 2005-047751 A | 2/2005 | |
| JP | 2005-050684 A | 2/2005 | |
| JP | 2005047751 A * | 2/2005 | ............ C01B 25/45 |
| JP | 2006302671 A | 11/2006 | |
| WO | WO-02/27823 A1 | 4/2002 | |
| WO | WO-02/27824 A1 | 4/2002 | |
| WO | WO-2005/051840 A1 | 6/2005 | |
| WO | WO-2005/062404 A1 | 7/2005 | |
| WO | WO 2008062111 A2 * | 5/2008 | |
| WO | WO-2009/079757 A1 | 7/2009 | |

OTHER PUBLICATIONS

Written Opinion (PCT/ISA/237) mailed on Apr. 21, 2011, by the Canadian Intellectual Property office as the International Searching Authority for International Application No. PCT/CA2011/000108. 5 pages.

English translation of the International Preliminary Report on Patentability, corresponding International Application No. PCT/CA2011/000108, dated Aug. 7, 2012.

Partial English translation of Office Action for corresponding Japanese Patent Application No. 2012-550278, dated Jul. 22, 2014.

Partial English translation of Office Action for corresponding Chinese Patent Application No. 201180007773.7, dated Aug. 8, 2014.

* cited by examiner

PROCEDURE TO OPTIMIZE MATERIALS FOR CATHODES AND CATHODE MATERIAL HAVING ENHANCED ELECTROCHEMICAL PROPERTIES

CROSS REFERENCE TO RELATED APPLICATIONS

This application is a continuation of U.S. application Ser. No. 13/575,917, filed on Jul. 27, 2012, which is a U.S. national stage application of International Application No. PCT/CA2011/000108, filed on Jan. 28, 2011, which claims the benefit of priority of Canadian Application No. 2,691,265, filed on Jan. 28, 2010, the content of which is incorporated here by reference in its entirety. The entire contents of each of U.S. application Ser. No. 13/575,917, International Application No. PCT/CA2011/000108, and Canadian Application No. 2,691,265 are hereby incorporated herein by reference in their entirety.

FIELD OF THE INVENTION

This invention concerns a method of optimization for cathode material that includes enhanced electrochemical properties. This invention also concerns a material that enjoys enhanced electrochemical properties.

DESCRIPTION OF THE PRIOR ART

The $LiCoO_2$ intercalation compound in lithium ion batteries contains very good electrochemical properties. However, the limited quantity, the price of cobalt, and safety problems hamper the generalization of using such Lithium-ion battery in applications that require high storage capacities. It has been proposed that the lithium and transition metal oxides be replaced by materials with an olivine isotope structure, more in particular of the $LiMPO_4$ type; where M may be a metal such as iron (Cf. U.S. Pat. No. 5,910,382 and U.S. Pat. No. 6,514,640). Safety problems are thus resolved, thanks to the covalent P—O bond which stabilizes the fully charged cathode versus the release of oxygen.

Certain materials, such as $LiFePO_4$, have suboptimal kinetics, induced by intrinsically weak electronic conductivity, which results from the fact that the $PO_4$ polyanions are covalently bonded. However, the use of a thin layer of pyrolytic carbon on the surface of such materials (as described in EP1049182, CA 2,307,119, U.S. Pat. No. 6,855,273, U.S. Pat. No. 6,962,666, U.S. Pat. No. 7,344,659, U.S. Pat. No. 7,457,018, WO 02/27823 & WO 02/27824) has allowed the us to development and marketing of a phosphate product bearing an electronically conductive pyrolytic carbon deposit (for example, C—$LiFePO_4$) in a high capacity battery grade that is able to provide high power. In the specific case of lithium and iron phosphate, this material can also be modified by partial replacement of the Fe cations with the metal isovalent or aliovalent cations, such as for example and without limitation, Mn, Ni, Co, Mg, Mo, Nb, Ti, Al, Ta, Ge, La, Y, Yb, Sm, B, Ce, Hf, Cr, Zr, Bi, Zn, Ca and W, or by partial replacement of the oxyanion $PO_4$ with $SiO_4$, $SO_4$ or $MoO_4$ (as described in U.S. Pat. No. 6,514,640).

In the specific case of C—$LiFePO_4$, the potential of the 3.5 V C—$LiFePO_4$ cathode vs. the $Li^+/Li°$ cathode (in fact also an ideal candidate for lithiated metal polymer (LMP) technology batteries) uses a lithium metal anode to replace the vanadium oxides. In fact, these batteries use a dry polymer of the polyether family as an ionic conducting electrolyte in which a lithium salt is dissolved, of which the electrochemical window of stability is about 4 V vs. $Li^+/Li°$. Using C—$LiFePO_4$ makes it possible to design LMP batteries for electric vehicles giving excellent cycling performance and improved safety.

SUMMARY OF THE INVENTION

It appeared that some batches of the lithiated or partially lithiated oxyanion-based materials comprising a deposit of pyrolytic carbon on its surface (particularly in cases where the material is C—$LiFePO_4$) posed specific problems when used as a cathode, for example in the specific case of a LMP battery, particularly regarding their electrochemical properties. Specifically, these problems were first identified by an increase in the area specific impedance (called "ASI" from the English "Area Specific Impedance") of the batteries, this increase being prejudicial to the battery performance.

These specific problems lead inventors to begin an R&D project which allowed them to identify and to solve this problem. Following many experiments with various illustrative and non-restrictive batches of C—$LiFePO_4$ material, the inventors noticed that, surprisingly, the ASI increase in LMP batteries was correlated with the presence of low levels of calcium-bearing impurities. No document of the prior art explains or suggests the negative effect of calcium-bearing impurities on the ASI of LMP batteries.

Consequently, this invention relates to a lithiated or partially lithiated oxyanion-based materials comprising a pyrolytic carbon deposit on the surface which presents improved electrochemical properties, such as for example, when used as a cathode in an LMP technology battery.

In a non-restrictive aspect, this invention also proposes an electrode containing the material defined above and the use of this electrode in an LMP technology battery.

In a non-restrictive aspect, this invention also proposes a C-$A_xM(XO_4)_y$ material consisting of particles of a compound with the formula $A_xM(XO_4)_y$, where the particles comprise a carbon deposit deposited by pyrolysis on at least part of its surface, where: A stands for Li, alone or partially replaced by more than 10% atomic percentage of Na or K; M stands for Fe(II), or Mn(II), or mixtures thereof, alone or partially replaced by more than 30% atomic percentage of one or more other metals chosen between Ni and Co, and/or by more than 10% atomic percentage of one or more aliovalent or isovalent metals other than Ni or Co, and/or by more than 5% atomic percentage of Fe(III); $XO_4$ stands for $PO_4$ alone or partially replaced by more than 10% atomic percentage of at least one group chosen from among $SO_4$, $SiO_4$ and $MoO_4$; $0<x\leq2$ and $0<y\leq2$, the coefficients x and y being chosen independently to ensure electroneutrality of the oxide complex; and where the material has a calcium level present as an impurity lower than approximately 1000 ppm.

In another non-restrictive aspect, this invention proposes a method for improving the electrochemical properties of a lithiated metal polymer (LMP) technology battery where the battery comprises a lithiated or partially lithiated oxyanion-based material comprising particles of a compound having the formula $A_xM(XO_4)_y$, where the particles comprise carbon deposited by pyrolysis on at least part of its surface, where: A stands for Li, alone or partially replaced by more than 10% atomic percentage of Na or K; M stands for Fe(II) or Mn(II), or a mixture thereof, alone or partially replaced by more than 30% atomic percentage of the atoms of one or more other metals chosen from Ni and Co, and/or by more than 10% atomic percentage of one or more aliovalent or isovalent metals other than Ni or Co, and/or by more than 5% atomic percentage of Fe(III); and $XO_4$ stands for $PO_4$ alone or partially replaced by more than 10% atomic percentage of at least one group chosen from among $SO_4$, $SiO_4$ and $MoO_4$; $0<x\leq2$ and $0<y\leq2$, the coefficients x and y being chosen independently to ensure electroneutrality of the oxide complex; and where the method comprises: (i) determination of the level of the calcium present as impurity (a) of a lithiated or partially lithiated oxyanion-based materials comprising the particles of a compound having the formula $A_xM(XO_4)_y$, (b) of a lithiated or partially lithiated oxyanion-based material comprising particles of a compound having the formula $A_xM(XO_4)_y$, where the particles comprise carbon deposited by pyrolysis on at least part of its surface, or (c) of the precursors of (a) or (b); and (ii) selected from among (a), (b) or (c) of the material or precursors containing a level of calcium as an impurity lower than approximately 1000 pm, preferably lower than approximately 500 ppm, even more preferably lower than approximately 300 ppm, even more preferably lower than approximately 100 ppm.

In one embodiment, the method defined above includes, during the synthesis of the materials and (or) during the washing stages, the use of water that is more or less calcareous so that the level of calcium present in the $C-A_xM(XO_4)_y$ product as an impurity will be lower than approximately 1000 ppm, preferably lower than approximately 500 ppm, even more preferably lower than approximately 300 ppm, even more preferably lower than approximately 100 ppm.

In one embodiment, the carbon film is a uniform, adherent, deposit that is not powdery. This represents approximately 0.03 to approximately 15% by weight, preferably approximately 0.5 to approximately 5% by weight in comparison to the total weight of the material. In one embodiment, the material of this invention, when used as material for a cathode, presents at least a charge/discharge plateau of approximately 3.4-3.5 V vs. $Li^+/Li^\circ$, characteristic of the $Fe^{+2}/Fe^{+3}$ couple.

In another non-restrictive aspect, this invention proposes an $MPO_4$ material, possibly hydrated, for the synthesis of the $C-LiMPO_4$ by a thermal process, where the material has a level of calcium present as an impurity lower than approximately 1000 ppm, M is a metal representing at least 70% atomic percentage of Fe(II). In one embodiment, the $MPO_4$ material for synthesis of $C-LiMPO_4$ by a thermal process, is characterized by a level of calcium present as an impurity lower than approximately 500 ppm, preferably lower than approximately 300 ppm, even more preferably lower than approximately 100 ppm.

In another non-restrictive aspect, the impurity comprising the calcium is essentially present on the surface of the $MPO_4$ material.

In one specific embodiment, M represents Fe(II), the $FePO_4$ material, possibly hydrated, for synthesis of $C-LiFeO_4$ by a thermal process, is characterized by a level of calcium present as an impurity lower than approximately 1000 ppm, preferably lower than approximately 500 ppm, preferably lower than approximately 300 ppm, even more preferably lower than approximately 100 ppm.

In another non-restrictive aspect, the impurity comprising the calcium is essentially present on the surface of the $FePO_4$ material.

These aspects and other characteristics of this invention will now be made apparent for the professional in the field by reviewing the following description of particular embodiments of the invention.

DESCRIPTION OF THE INVENTION

Following numerous experiments, the inventors observed that, surprisingly, the increase of ASI in LMP batteries was correlated to the presence of calcium bearing-impurities.

In one non-restrictive embodiment of this concept, the inventors used $C-LiFePO_4$ synthesized by a solid-state thermal process. This solid-state thermal process consists of mixing sources of Li, Fe, and $PO_4$ with an organic compound. More specifically, lithium carbonate ($Li_2CO_3$), iron phosphate ($FePO_4$), and a polymer are mixed, and then heated in a reducing atmosphere in a rotating kiln, and upon exiting therefrom, a $C-LiFePO_4$ cathode material is obtained. In this specific example, the inventors correlated the origin of the calcium present as an impurity from the first material $FePO_4$, as being able to contain calcium-bearing impurities, in particular calcium phosphates or calcium carbonates which are poorly soluble in an aqueous medium. These calcium-bearing impurities are found in fine in the $C-LiFePO_4$ product.

In this non-restrictive embodiment, the inventors observed an increase in the ASI during the cycling of LMP batteries. The batches of $C-LiFePO_4$ only contained low amounts of calcium present as an impurity, that is to say, only a few hundred ppm as determined by chemical microanalyses (plasma gun, etc.). One can advance explanations for this surprising effect, without this being a limiting factor on the invention. During the manufacture of certain $FePO_4$ batches, it is possible to use calcareous water during synthesis and/or during washing phases which leads to the deposit of poorly water soluble calcium salts, in particular calcium carbonates and phosphates (for example $CaHPO_4$, $Ca_3(PO_4)_2$, $CaCO_3$, etc.), on the surface of $FePO_4$ used as the raw material for synthesizing the product $C-LiFePO_4$. It could be assumed that this calcium present as an impurity is found completely or partially on the surface of $C-LiFePO_4$, for example, but without restriction, in the form of calcium phosphate, which may contain lithium or not. XPS analysis of the surface of $C-LiFePO_4$ containing calcium present as an impurity confirmed its presence on the surface of the material.

The observation of the harmful effects of the presence of calcium as an impurity in LMP technology can be explained by the very strong viscosity of the electrolyte, in contrast to a liquid electrolyte, involving the formation of an interface which limits the ionic transfers between the electrolyte and cathode. Moreover, since the polymeric electrolyte based on polyether has a strong capacity as a solvent, it may be assumed, without this being a restriction in any way on the invention, that the calcium-based impurities interact or are at least partially solubilized thereby. This effect may be reinforced by using the lithium salt of bis(trifluoro-methanesulfonyl)imide (called "LiTFSI") currently used as electrolytes in LMP batteries, in fact, the TFSI anion is capable of taking many cations in solution, including divalent cations such as calcium. A polymer electrolyte is a conductor which, if it has an amorphous structure, i.e., a disorganized structure, is the only structure capable of disassociating and dissolving the salt. Any crystal growth primer will cause an increase in the cohesion energy of polymer and has harmful consequences for the ionic conductivity of the material. Such an amorphous structure is only obtained by placing it at a temperature higher than the glass transition temperature $T_g$, which must thus be the lowest possible. The value of $T_g$ can change, depending on the amount of the salt solvate in the polymer, and also depending on the nature of the cation for a given anion. An impurity containing the divalent calcium present on the surface of the material $C-A_xM(XO_4)_y$, can thus increase the glass transition temperature of the electrolyte locally at the interface with the electrolyte, so that compounds defined as microcrystalline are formed at the high melting point, resulting in an increase in the resistance of the interfaces and thus in the ASI.

This is why, in one particular embodiment, the method of the invention comprises, during the synthesis of the materials and (or) during the washing stages, the use of water that is more or less calcareous so that the level of calcium present in the $C\text{-}A_xM(XO_4)_y$ product as an impurity will be lower than approximately 1000 ppm, preferably lower than approximately 500 ppm, more preferably lower than approximately 300 ppm, even more preferably lower than approximately 100 ppm, The professional in the field will be able to obtain a water which is weakly or not calcareous without any extra effort.

The purpose of the many experiments reported here was thus to identify the causes of the unexpected degradation in batteries performances using $C\text{—}LiFePO_4$ batches which are in principle, similar and to identify an optimized compound for lithiated metal polymer technology batteries containing the material $C\text{-}A_xM(XO_4)_y$.

In one particular embodiment, the material of this invention, designated in this descriptive memory as the "$C\text{-}A_xM(XO_4)_y$ material", is constituted by particles of a compound having the formula $A_xM(XO_4)_y$ which has an olivine structure and that carries on at least part of its surface, carbon deposited by pyrolysis, where:

A stands for Li, alone or partially replaced by more than 10% atomic percentage of Na or K;

M stands for Fe(II) or Mn(II), or a mixture thereof, alone or partially replaced by more than 30% atomic percentage of the atoms of one or more other metals chosen from Ni and Co, and/or by more than 10% atomic percentage of one or more aliovalent or isovalent metals other than Ni or Co, and/or by more than 5% atomic percentage of Fe(III); and $XO_4$ is an oxyanion and stands for $PO_4$ alone or partially replaced by more than 10% atomic percentage of at least one group chosen from among $SO_4$, $SiO_4$ and $MoO_4$;

$0 < x \leq 2$ and $0 < y \leq 2$, the coefficients x and y being chosen independently to ensure electroneutrality of the oxide complex;

the material being characterized in that it has a level of calcium present as an impurity lower than approximately 1000 ppm.

In one particular embodiment, the material $C\text{-}A_xM(XO_4)_y$ above is characterized in that it has a content of calcium present as an impurity lower than approximately 500 ppm, preferably less than approximately 300 ppm, and even more preferably lower than approximately 100 ppm.

In a $2^{nd}$ particular embodiment, the material $C\text{-}A_xM(XO_4)_y$ of this invention is constituted by particles of a compound with the formula $A_xM(XO_4)_y$ which has an olivine structure and that carries on at least part of its surface, carbon deposited by pyrolysis, where:

A stands for Li, alone or partially replaced by more than 10% atomic percentage of Na or K;

M stands for Fe(II), alone or partially replaced by more than 30% atomic percentage of the atoms of one or more other metals chosen from Mn, Ni and Co, and/or by more than 10% atomic percentage of one or more aliovalent or isovalent metals chosen from Mg, Mo, Nb, Ti, Al, Ta, Ge, La, Y, Yb, Sm, Ce, Cu, Hf, Cr, Zr, Bi, Zn, B, Ca, and W, and/or by more than 5% atomic percentage of Fe(III); and $XO_4$ is an oxyanion and stands for $PO_4$ alone or partially replaced by more than 10% atomic percentage of at least one group chosen from among $SO_4$, $SiO_4$ and $MoO_4$;

$0 < x \leq 2$ and $0 < y \leq 2$, the coefficients x and y being chosen independently to ensure electroneutrality of the oxide complex, the material being characterized in that it has a level of calcium present as an impurity lower than approximately 1000 ppm.

In one particular embodiment, the material $C\text{-}A_xM(XO_4)_y$ above is characterized in that it has a content of calcium present as an impurity lower than approximately 500 ppm, preferably lower than approximately 300 ppm, even more preferably lower than approximately 100 ppm, In a $3^{rd}$ particular embodiment, the material $C\text{-}A_xM(XO_4)_y$ is $C\text{—}LiMPO_4$ constituted by particles of a compound with the formula $LiMPO_4$ which has an olivine structure and that carries on at least part of its surface, carbon deposited by pyrolysis, M stands for at least 70% atomic percentage of Fe(II), and is characterized in that it has a level of calcium present as an impurity lower than approximately 1000 ppm, preferably lower than approximately 500 ppm, preferably lower than approximately 300 ppm, and even more preferably lower than approximately 100 ppm.

In a $4^{th}$ particular embodiment, the material $C\text{-}A_xM(XO_4)_y$ is $C\text{—}LiFePO_4$ constituted by particles of a compound with the formula $LiFePO_4$ which has an olivine structure and that carries on at least part of its surface, carbon deposited by pyrolysis, and is characterized in that it has a level of calcium present as an impurity lower than approximately 1000 ppm, preferably lower than approximately 500 ppm, preferably lower than approximately 300 ppm, and even more preferably lower than approximately 100 ppm.

The level of calcium present as an impurity of a material according to the invention may be measured by using equipment currently used in the industry, in particular plasma guns, which make it possible to perform chemical microanalyses (inductive coupling plasma spectrometry, etc.), for example, like the ICP spectrometers from the Horiba Scientific company. The analysis frequently consists of wet mineralization, by sample acid dissolution, then the solution obtained is injected into the plasma in the form of an aerosol. The level of the different elements is determined afterwards using detectors based on optical emission spectrometry or mass spectrometry.

The properties of the material according to the invention may be adapted by appropriately choosing element(s) to partially replace Fe. For example, in a material in which the oxide complex has the formula $LiFe_{1-(x+y)}M'_xM''_yPO_4$, the choice of M' from Mn, Ni, and Co makes it possible to adjust the discharge potential of the cathode material. The choice of M'' from, for example, Mg, Mo, Nb, Ti, Al, B, Zr, Ca and W may allow the kinetic properties of the cathode material to be adjusted.

Among the materials of the invention, those in which the oxide complex $A_xM(XO_4)_y$ has the formula $LiFe_{1-(x+y)}M'_xM''_yPO_4$, with $x+y \leq 0.3$, are particularly preferred.

Within the context of this invention, the expression, "particles" encompasses either the elementary particles or the agglomerates made up of the elementary particles, as well as the so-called secondary particles. The size of the elementary particles should be preferably between 10 nm and 3 μm. The size of the agglomerate particles should be preferably between 100 nm and 30 μm. These particle sizes and the presence of the carbon deposit confer a specific raised surface to the material, which is typically between 5 and 50 m²/g.

In one particular embodiment of the invention, the material $C\text{-}A_xM(XO_4)_y$ is comprised of primary particles of a micron size, mainly more than approximately 1 μm and preferably between approximately 1 μm and approximately 5 μm. The size of the secondary particles should be preferably between 1 μm and approximately 10 μm.

In another particular embodiment of the invention, the C-$A_xM(XO_4)_y$ material is comprised of primary particles with a distribution of particle sizes $D_{50}$ ranging from approximately 1 μm and approximately 5 μm, and so that the distribution of size of the secondary particles $D_{50}$ ranges from between approximately 1 μm and approximately 10 μm.

In another particular embodiment of the invention, the material C-$A_xM(XO_4)_y$ is characterized in that the size of the elementary particles ranges between 10 nm and 3 μm and the size of the agglomerate particles ranges between 100 nm and 30 μm.

The material C-$A_xM(XO_4)_y$ may be prepared using several methods. It may be obtained for example by hydrothermal processing (Cf. WO 05/051840), by solid state heat processing (Cf. WO 02/027823 and WO 02/027824), or by melting (Cf. WO 05/062404).

In one preferred mode of synthesis for the material C-$A_xM(XO_4)_y$, synthesis is implemented by creating a reaction by placing into a gas atmosphere a balanced, thermodynamic and kinetic mixture in the proportions required from sources of the following compounds (a), (b), (c), (d) and (e), including:
a) one or more sources of the compounds of the element(s) making up A;
b) one or more sources of the element(s) making up M;
c) a source compound of the element(s) X;
d) a source compound for oxygen; and
e) a source compound of the conductor carbon;

the synthesis is carried out continuously in a kiln while controlling the composition of the gaseous atmosphere, the temperature of the synthesizing reaction and the level of the source compound c) relative to the other source compounds a), b), d), and e), in order to set the state of oxidation of the transition metal to the degree of the valence desired to constitute the compound of the $A_xM(XO_4)_y$ type the method comprising a compound pyrolysis stage e).

In this embodiment, the gas flow and the flow of solid products circulating crosscurrent, under optimal conditions, the material C-$A_xM(XO_4)_y$ recovered upon exiting the kiln, contains less than approximately 200 ppm of water.

In one particular mode of synthesis, the source compound a) is for example, a lithium compound chosen from the group made up by lithium oxide or hydroxide, lithium carbonate, the neutral phosphate $Li_3PO_4$, the acid phosphate $LiH_2PO_4$, the orthosilicates, the metasilicates, or polysilicates of lithium, lithium sulfate, lithium oxalate and lithium acetate, and a mixture of any of these. The source compound b) is for example, an iron compound chosen from the group made up by iron(III) oxide or magnetite, trivalent iron phosphate, iron hydroxyphosphate and lithium hydroxyphosphate or trivalent iron nitrate, iron phosphate, vivianite, hydrated or not, $Fe_3(PO_4)_2$, iron acetate $(CH_3COO)_2Fe$, iron sulfate ($FeSO_4$), iron oxalate, iron and ammonium phosphate ($NH_4FePO_4$), and a mixture of any of these. The source compound c) is a phosphorus compound chosen for example, from the group made up by phosphoric acid and its esters, the neutral phosphate $Li_3PO_4$, the acid phosphate $LiH_2PO_4$, the mono- or di-ammonium phosphates, trivalent iron phosphate, manganese and ammonium phosphate ($NH_4MnPO_4$). All these compounds are also a source of oxygen and certain of these are sources of at least two elements from among Li, Fe, and P. The deposit of carbon on the surface of particles of the oxide complex $A_xM(XO_4)_y$ is obtained by pyrolysis from a source compound e). Pyrolysis of the compound e) may be performed at the same time as the synthesis reaction between the compounds a) to d) to form the compound $A_xM(XO_4)_y$. It may also be performed in a stage following the synthesis reaction.

The deposit of a layer of conducting carbon on the surface of the oxide complex particles $A_xM(XO_4)_y$ may be obtained by thermal decomposition of source compounds e) which may be very wide-ranging. An appropriate source compound is a compound that is in the liquid or gaseous state, a compound that may be used in the form of a solution in a liquid solvent, or a compound that passes to the liquid or gaseous state during the course of its thermal decomposition, so that it may be more or less completely covered by the oxide complex particles.

The source compound e) may for example, be chosen from a group made up by liquid, solid, or gaseous hydrocarbons, and their derivatives (in particular the polycylic aromatic species such as tar or pitch), perylene and their derivatives, polyhydric compounds (for example sugars and carbohydrates, and their derivatives), polymers, cellulose, starches and their esters and ethers, and a mixture of any of these. As an example of polymers, the polyolefins may be mentioned, as well as polybutadiens, polyvinyl alcohol, polyvinyl butyral, condensation products of phenols (and comprising those obtained through an aldehyde reaction), polymers derived from furfurylic alcohol, styrene, divinylbenzene, naphthalene, perylene, acrylonitrile, and vinyl acetate.

When the compound e) is CO or a gaseous hydrocarbon, it is submitted to a dismutation, advantageously catalyzed by a transition metal element present in at least one of the precursors a) to c), or by a transition metal compound added to the precursor mixture.

When the source compound e) is a gas or a gas mixture such as ethylene, propylene, acetylene, butane, 1,3 butadiene, or 1-butene, thermal decomposition is performed by cracking in an oven at a temperature of between approximately 100 and approximately 1300° C., and more in particular between approximately 400 and approximately 1200° C., preferably in the presence of an inert carrier gas. (Cf. for example US 2002/195591 and US 2004/157126).

The carbon deposit may also be performed by CVD from hydrocarbons as described in JP 2006-302671.

In one particular mode of synthesis, the material C—$LiFePO_4$ is prepared by a solid state thermal process from iron phosphate ($FePO_4$), lithium carbonate ($Li_2CO_3$) and an organic carbon source compound.

A material C-$A_xM(XO_4)_y$ in accordance with the invention is particularly useful as a cathode in a lithiated metal polymer technology battery (LMP), using a metal lithium anode and a solid polymer electrolyte which may be plastic or not.

In one particular embodiment, the cathode is preferably constituted of a composite material applied on a collector, the composite material comprising C-$A_xM(XO_4)_y$, a polymer solvent which may be salified or not as a binder, preferably the electrolyte solvent will be made of a polymer, and a material which favors electronic conduction. The material favoring electronic conduction is chosen advantageously from among a group including lampblack (Ketjenblack, etc.), graphite, carbon fibers (for example, in the form of carbon nanotubes or VGCF carbon fibers (Vapor Grown Carbon Fiber) the growth of the carbon nanotubes and the graphene is carried out in the gaseous phase.

The polymer solvent is advantageously chosen from among the polymers comprising polyether segments, the dissolution of a lithium salt in this polymer makes it possible to prepare a solid polymer electrolyte. As examples of polyethers that may be used within the context of this invention to form the electrolyte, poly(ethylene oxide) may be mentioned, and copolymers that are obtained from ethylene oxide and at least one substituted oxyrane, and which includes at least 60% recurrent units of —$CH_2$—$CH_2O$— derived from ethylene oxide. The recurrent units derived from a substituted oxyrane may be from —O—CH$_2$—CHR— units (derivatives of a oxyrane CH$_2$—CHR—O) in which R is a radical alkyl, chosen preferably from radical alkyls having between 1 and 16 carbon atoms, more preferably from radical alkyls having between 1 and 8 carbon atoms. The recurrent units derived from a substituted oxyrane may also be from —O—CH$_2$—CHR'— units (derivatives of an oxyrane CH$_2$—CHR'—O) in which R' is a group capable of radical polymerization. Said group may be chosen from among those comprising a double bond, for example, a vinyl, allyl, vinylbenzyl, or acryloyl group. As examples of these groups, groups having the formula CH$_2$=CH—(CH$_2$)$_q$—(O—CH$_2$)$_p$— with 1<q<6 et p=0 or 1 may be mentioned, or the formula CH$_3$—(CH$_2$)$_y$—CH=CH—(CH$_2$)$_x$—(OCH$_2$)$_p$—, with 0<x+y<5 and p=0 or 1. A polyether which is useful in this invention may contain recurrent units derived from various substituted oxyranes. In one embodiment, the polyether used according to this invention, consists of recurrent units derived from at least one substituted oxyrane in which the substituent includes a polymerizing function. As an example, allyl glycidyl ether may be mentioned.

The polymer electrolyte may also be constituted by a mixture of polymers, for example, but without limitation, by the mixture of a polymer solvent and of a polymer non-solvent and/or at least partially soluble in the polymer solvent (Cf. FR 2,881,275 and WO 2009/079757).

In one particular embodiment, the lithium salt may be chosen specifically from among LiPF$_6$, LiAsF$_6$, LiClO$_4$, LiBF$_4$, LiC$_4$BO$_8$, Li(C$_2$F$_5$SO$_2$)2N, Li[(C$_2$F$_5$)$_3$PF$_3$], LiCF$_3$SO$_3$, LiCH$_3$SO$_3$, LiN(SO$_2$F) and LiN(SO$_2$CF$_3$)$_2$.

The polymer electrolyte thus formed, may optionally be plasticized by at most 30% by weight of a liquid solvent, a plasticizer or a polymer of low mass.

The capacity of the cathode is currently expressed in mg of electroactive material per cm$^2$ of the cathode's surface.

The cathode is created from a C-A$_x$M(XO$_4$)$_y$ material from this invention having a level of calcium present as an impurity lower than approximately 1000 ppm, preferably lower than approximately 500 ppm, preferably lower than around 300 ppm, even more preferably lower than approximately 100 ppm.

A C—LiFePO$_4$ material and a C—LiMPO$_4$ material wherein M stands for at least 70% atomic percentage of Fe partially replaced by Mn, Nb or Mg are especially preferred as the active material of the cathode.

The above is considered as an illustration of the principles of the invention. Furthermore, since numerous modifications and changes may be apparent to the professional in the field, it is not desirable to limit the invention to the precise examples and embodiments shown and described, and, consequently, all appropriate an equivalent modifications may be invoked as connected to the scope of the invention.

EXAMPLES

The method according to the invention has been implemented in a comparative fashion with the techniques of the prior art, in order to show that a very low level of calcium present as an impurity has a favorable effect on the performance of the material C-A$_x$M(XO$_4$)$_y$ used as the material of the cathode in a lithiated metal polymer technology battery.

Example 1

Synthesis of C—LiFePO$_4$ by a Solid State Thermal Method

A mixture is prepared containing FePO$_4$•(H$_2$O)$_2$ (1 mole) and Li$_2$CO$_3$ (1 mole, level of purity: 99.9%), and 5% poly-ethylene-block-poly(ethylene glycol) containing 50% ethylene oxide, which is introduced into isopropyl alcohol and it is stirred for approximately 10 hr, then the solvent is removed. In the material thus obtained, the polymer retains the phosphate and carbonate particles together.

The mixture is treated under a stream of nitrogen at 700° C. for 2 hours, to obtain a battery grade C—LiFePO$_4$ material, then it is vacuum dried at 100° C. and the final material is stored in a glove box in an argon atmosphere with dew point set at –90° C. The material has a specific surface of 13.4 m$^2$/g and a carbon level of 1.7% by weight.

This synthesis is repeated with selected batches of FePO$_4$ containing more or less impurity as calcium, the table below giving the calcium (Ca) levels determined by microanalysis (plasma gun) in the final C—LiFePO$_4$ product.

| C-LiFePO$_4$ Samples | Ca level in C-LiFePO$_4$ (ppm) |
|---|---|
| A | 52 |
| B | 260 |
| C | 1100 |
| D | 3200 |

These syntheses were repeated with batches of FePO$_4$ in which the Fe(II) is substituted by 5% atomic percentage with respect to the magnesium (Mg) and manganese (Mn), and containing calcium present as an impurity. The table below gives the calcium (Ca) levels determined by microanalyses (plasma gun) in the final C—LiFe$_{0.95}$Mg$_{0.05}$PO$_4$ and C—LiFe$_{0.95}$Mn$_{0.05}$PO$_4$ products.

| Samples C-LiFe$_{0.95}$Mg$_{0.05}$PO$_4$ | Ca Level in C-LiFe$_{0.95}$Mg$_{0.05}$PO$_4$ (ppm) | Samples C-LiFe$_{0.95}$Mn$_{0.05}$PO$_4$ | Ca Level in C-LiFe$_{0.95}$Mn$_{0.05}$PO$_4$ (ppm) |
|---|---|---|---|
| A-Mg | 45 | A-Mn | 66 |
| B-Mg | 320 | B-Mn | 300 |
| C-Mg | 1200 | C-Mn | 1050 |
| D-Mg | 2950 | D-Mn | 3050 |

Example 2

Preparation of Lithiated Metal Polymer Batteries

In the different assembled batteries in this example, the cathodes are created with the C—LiFePO$_4$ cathode materials obtained in example 1. The LMP batteries were prepared according to the following operational mode. 2.06 g of C—LiFePO$_4$, 1.654 g de poly(ethylene oxide), having a molecular mass of 100,000, and 334 mg Ketjenblack carbon powder (furnished by Akzo-Nobel), was carefully mixed for 1 hour, in acetonitrile, using a Turbula® mixer with zircon balls. The mixture obtained was then placed on a sheet of aluminum foil with a carbonized coating (supplied by Exopack Advanced Coatings™), using a Gardner® device, the film deposited was vacuum dried at 80° C. for 12 hours, then stored in a glove box. The cathodes contained 4 mg/cm$^2$ of C—LiFePO$_4$.

Batteries A1, B1, C1, and D1 ("button" type battery), were assembled and sealed in the glove box for each of samples A, B, C, and D, by using the carbonated sheets of aluminum foil with the coating containing these phosphates as a cathode, a lithium metal film as an anode and a poly(ethylene oxide) film containing 30% by weight of LiTFSI (supplied by the 3M company).

The batteries A1, B1, C1, and D1 were submitted to intentiostatic cycling at a regime of C/4 at 80° C. between 2 and 3.8 Volts vs. Li$^+$/Li$^\circ$. The ASI was determined at the beginning of discharge in a C/4 regime by the current interruption method being used (1 second in this case), and in the 5$^{th}$ and 100$^{th}$ cycle. The results indicated (ASI in Ohm cm$^2$) in the table below confirming the harmful role of calcium present as an impurity in C—LiFePO$_4$ used as a cathode in a lithiated metal polymer technology battery.

| C-LiFePO$_4$ Samples | ASI 5$^{th}$ cycle | ASI 100$^{th}$ cycle |
|---|---|---|
| A | 161 | 164 |
| B | 162 | 195 |
| C | 161 | 302 |
| D | 163 | 604 |

The A1-Mg, B1-Mg, C1-Mg, and D1-Mg batteries and respectively A1-Mn, B1-Mn, C1-Mn, and D1-Mn ("button" type battery) were assembled and sealed in a glove box for each of the A-Mg, B-Mg, C-Mg, et D-Mg samples and respectively A-Mn, B-Mn, C-Mn, and D-Mn, by using the carbonated sheets of aluminum foil with the coating containing these phosphates as a cathode, a lithium metal film as an anode and a poly(ethylene oxide) film containing 30% by weight of LiTFSI (supplied by the 3M company).

These batteries were characterized as identical to the A1, B1, C1 and D1 batteries, a similar increase in the ASI could be seen in correlation with the amount of calcium present as an impurity.

Although the invention has been described in detail in reference to certain embodiments thereof, variations and improvements are possible without going outside the spirit of the invention. All the materials and (or) the methods described and claimed here may be formulated and executed without excessive experimentation in the light of the invention. Although the materials and the methods of this invention have been described in terms of the preferred embodiments, it will be evident for the professional in the field that variations may be applied to the materials and (or) the methods of the stages or in the sequence of the stages of the method described above without going outside the concept, the spirit, and the scope of the invention. Any substitutes of the same kind and modifications which may become apparent to the professional in the field shall be noted as being within the spirit, the scope, and the concept of the invention as defined by the Claims here attached.

All references cited in this document are herein incorporated by reference in their entirety.

The invention claimed is:

1. A material C-A$_x$M(XO$_4$)$_y$, consisting of particles of a compound with the formula A$_x$M(XO$_4$)$_y$, where the particles comprise a carbon deposit deposited by pyrolysis on at least part of its surface, wherein:
    A stands for Li, alone or partially replaced by at most 10% atomic percentage of Na or K;
    M stands for Fe(II) or Mn(II), or mixtures thereof, alone or partially replaced by at most 30% atomic percentage of the atoms of one or more other metals chosen from Ni and Co, and/or by at most 10% atomic percentage of one or more aliovalent or isovalent metals other than Ni or Co, and/or by at most 5% atomic percentage of Fe(III); and
    XO$_4$ stands for PO$_4$ alone or partially replaced by at most 10% atomic percentage of at least one group chosen from among SO$_4$, SiO$_4$, and MoO$_4$; and
    0<x≤2 and 0<y≤2, the coefficients x and y being chosen independently to ensure electroneutrality of the oxide complex,
    and wherein the material has a level of calcium present as an impurity lower than approximately 1000 ppm, said calcium being principally deposited on the surface of the material C-A$_x$M(XO$_4$)$_y$.

2. Material according to claim 1, wherein M stands for Fe(II), alone or partially replaced by at most 30% atomic percentage of the atoms of one or more other metals chosen from Mn, Ni and Co, and/or by at most 10% atomic percentage of one or more aliovalent or isovalent metals chosen from Mg, Mo, Nb, Ti, Al, Ta, Ge, La, Y, Yb, Sm, Ce, Cu, Hf, Cr, Zr, Bi, Zn, B, Ca, and W, and/or by at most 5% atomic percentage of Fe(III).

3. Material according to claim 1, wherein the carbon deposit is a uniform, adherent, deposit that is not powdery.

4. Material according to claim 1, wherein the carbon deposit represents approximately 0.03 to approximately 15% by weight with respect to the total weight.

5. Material according to claim 1, wherein the calcium present as an impurity is principally in the form of a calcium phosphate, which optionally contains lithium.

6. Material according to claim 1, wherein the material C-A$_x$M(XO$_4$)$_y$ is C—LiFePO$_4$.

7. Material according to claim 1, being made up of the elementary particles and the agglomerates of the elementary particles.

8. Material according to claim 7, wherein the size of the elementary particles ranges between 10 nm and 3 μm, and the size of the agglomerate particles ranges between approximately 100 nm and approximately 30 μm.

9. Material according to claim 8, having a specific surface between approximately 5 m$^2$/g and approximately 50 m$^2$/g.

10. Material according to claim 7, wherein the size of the elementary particles ranges between approximately 1 μm and approximately 5 μm.

11. Material according to claim 7, wherein the size of the agglomerates ranges between approximately 1 μm and approximately 10 μm.

12. Material according to claim 1, wherein the material C-A$_x$M(XO$_4$)$_y$ is constituted by elementary particles and agglomerates of the elementary particles, where the elementary particles have a distribution of particle sizes D$_{50}$ falling between approximately 1 μm and approximately 5 μm, and where the agglomerates have a distribution of particle sizes D$_{50}$ falling between approximately 1 μm and approximately 10 μm.

13. Electrode constituted by a film of composite material deposited on a conductor substrate forming a current collector, wherein the composite material comprises the C-A$_x$M (XO$_4$)$_y$ material according to claim 1, a binder and an electronic conductor.

14. Electrode according to claim 13, wherein the binder is a polymer made up of at least 60% of recurrent units —CH$_2$—CH$_2$O— derived from ethylene oxide, in which a lithium salt is optionally dissolved.

15. Electrode according to claim 14, wherein when the lithium salt is present, this salt comprises LiN(SO$_2$CF$_3$)$_2$.

16. Battery comprising an anode, a cathode, and a polymer electrolyte containing a lithium salt, wherein the cathode comprises the material according to claim 1.

17. Battery according to claim 16, of the lithiated metal polymer technology (LMP).

18. Battery according to claim 16, wherein the electrolyte is a polymer made up of at least 60% of recurrent units —$CH_2$—$CH_2O$— derived from ethylene oxide, in which a lithium salt is dissolved.

19. Battery according to claim 18, wherein the lithium salt comprises $LiN(SO_2CF_3)_2$.

20. Battery according to any of claims 16 to 19, wherein the anode is of lithium metal.

21. An $MPO_4$ material, optionally hydrated, for synthesis of C—$LiMPO_4$ by a thermal process, M standing for at least 70% atomic percentage of Fe(II), wherein the material has a level of calcium present as an impurity lower than around 1000 ppm, and wherein the calcium present as an impurity is principally deposited on its surface.

22. Material according to claim 21, wherein the calcium present as an impurity is principally in the form of a calcium phosphate, which optionally contains lithium.

23. An $FePO_4$ material, optionally hydrated, for synthesis of C—$LiFeO_4$ by a thermal process, wherein the material has a level of calcium present as an impurity lower than approximately 1000 ppm, and wherein the calcium present as an impurity is principally deposited on its surface.

24. Method for improving the electrochemical properties of a lithiated metal polymer (LMP) technology battery, comprising one anode, one cathode, and a polymer electrolyte containing a lithium salt, where the cathode comprises a C-$A_xM(XO_4)_y$ material, said method comprising:
  (i) a determination of the level of calcium present as an impurity:
    (a) in a lithiated or partially lithiated oxyanion-based material comprising particles of a compound having the formula $A_xM(XO_4)_y$,
    (b) in a lithiated or partially lithiated oxyanion-based material comprising particles of a compound having the formula $A_xM(XO_4)_y$, where the particles comprise carbon deposited by pyrolysis on at least part of its surface, or
    (c) the precursors of (a) or (b);
  (ii) a selection from among (a), (b), or (c) of the material or precursors containing a level of calcium present as an impurity lower than approximately 1000 ppm to be used for manufacture of the C-$A_xM(XO_4)_y$ material for said one cathode, said C-$A_xM(XO_4)_y$ material having a level of calcium present as an impurity lower than approximately 1000 ppm, said calcium being principally deposited on the surface of the material C-$A_xM(XO_4)_y$, and wherein:
    A stands for Li, alone or partially replaced by at most 10% atomic percentage of Na or K;
    M stands for Fe(II) or Mn(II), or mixtures thereof, alone or partially replaced by at most 30% atomic percentage of the atoms of one or more other metals chosen from Ni and Co, and/or by at most 10% atomic percentage of one or more aliovalent or isovalent metals other than Ni or Co, and/or by at most 5% atomic percentage of Fe(III); and
    $XO_4$ stands for $PO_4$ alone or partially replaced by at most 10% atomic percentage of at least one group chosen from among $SO_4$, $SiO_4$, and $MoO_4$; and
    $0<x\leq2$ and $0<y\leq2$, the coefficients x and y being chosen independently to ensure electroneutrality of the oxide complex.

* * * * *